United States Patent
Burioni et al.

(10) Patent No.: US 10,011,648 B2
(45) Date of Patent: Jul. 3, 2018

(54) HUMAN MONOCLONAL ANTIBODY AGAINST THE VP1 PROTEIN OF JC VIRUS

(71) Applicant: POMONA RICERCA S.r.l., Turin (IT)

(72) Inventors: Roberto Burioni, Milan (IT); Massimo Clementi, Milan (IT)

(73) Assignee: POMONA RICERCA S.r.l., Turin (IT)

(*) Notice: Subject to any disclaimer, the term of this patent is extended or adjusted under 35 U.S.C. 154(b) by 247 days.

(21) Appl. No.: 14/410,896

(22) PCT Filed: Jun. 26, 2013

(86) PCT No.: PCT/IB2013/055257
§ 371 (c)(1),
(2) Date: Dec. 23, 2014

(87) PCT Pub. No.: WO2014/002035
PCT Pub. Date: Jan. 3, 2014

(65) Prior Publication Data
US 2015/0191530 A1     Jul. 9, 2015

(30) Foreign Application Priority Data

Jun. 27, 2012 (IT) .............................. TO2012A0570

(51) Int. Cl.
  *C07K 16/08* (2006.01)
  *G01N 33/569* (2006.01)
  *A61K 39/00* (2006.01)

(52) U.S. Cl.
  CPC .......... *C07K 16/081* (2013.01); *C07K 16/084* (2013.01); *G01N 33/56983* (2013.01); *A61K 2039/505* (2013.01); *C07K 2317/21* (2013.01); *C07K 2317/30* (2013.01); *C07K 2317/33* (2013.01); *C07K 2317/34* (2013.01); *C07K 2317/55* (2013.01); *C07K 2317/76* (2013.01); *G01N 2469/10* (2013.01)

(58) Field of Classification Search
None
See application file for complete search history.

(56) References Cited

U.S. PATENT DOCUMENTS

| 4,946,778 A | 8/1990 | Ladner et al. | |
| 2004/0259767 A1 | 12/2004 | Nagashima et al. | |
| 2015/0050271 A1* | 2/2015 | Simon ................... | C07K 16/084 424/133.1 |
| 2015/0056188 A1* | 2/2015 | Simon ................... | C07K 16/084 424/133.1 |

FOREIGN PATENT DOCUMENTS

| JP | 9-067397 A | 3/1997 | |
| WO | WO 97/19174 A1 | 5/1997 | |
| WO | WO 2013/142300 A2 | 9/2013 | |
| WO | WO 2014/002035 | * 1/2014 | ............ C07K 16/08 |

OTHER PUBLICATIONS

Aoki et al. (Neuroscience Letters, 1996, p. 111-114).*
Wang et al. (Journal of Virological Methods, 1999, vol. 78, p. 171-176).*
Knowles et al. (Journal of Virological Methods, 2003, vol. 109. p. 47-54).*
Bloomgren, G. et al., "Risk of Natalizumab-Associated Progressive Multifocal Leukoencephalopathy", *New England Journal of Medicine*, 366: 1870-1880 (2012).
Viscidi, R. et al., "Chapter 5: Serological Cross Reactivity between Polyomavirus Capsids", *Advances in Experimental Medicine and Biology*, 577: 73-84 (2006).
Knowles, W., "Chapter 2: Discovery and Epidemiology of the Human Polyomaviruses BK Virus (BKV) and JC Virus (JCV)", *Advances in Experimental Medicine and Biology*, 577: 19-45 (2006).
Ward, E.S. et al., "Binding activities of a repertoire of single immunoglobulin variable domains secreted from *Escherichia coli*", *Nature*, 341: 544-546 (1989).
Plaisant, P. et al., "Human monoclonal recombinant Fabs specific for HCV antigens obtained by repertoire cloning in phage display combinatorial vectors", *Res. Virol.*, 148: 165-169 (1997).
Williamson, R.A. et al., "Human monoclonal antibodies against a plethora of viral pathogens from single combinatorial libraries", *Proc. Natl. Acad. Sci. USA*, 90: 4141-4145 (1993).
International Search Report for corresponding International Patent Application No. PCT/IB2013/055257 dated Jun. 26, 2013.
Youssef, L. et al., "Anti-JCV Neutralizing Antibodies as a Potential Therapy for the Treatment of PML", *Journal of Neurovirology*, 18(1): 125 (2012).
Randhawa, P. et al., "Identification of species-specific and cross-reactive epitopes in human polyomavirus capsids using monoclonal antibodies", *Journal of General Virology*, 90(3): 634-639 (2009).
Goldmann, C. et al., "Molecular Cloning and Expression of Major Structural Protein VP1 of the Human Polyomavirus JC Virus: Formation of Virus-like Particles Useful for Immunological and Therapeutic Studies", *Journal of Virology*, 73(5): 4465-4469 (1999).
Atwood, W., "A combination of low-dose chlorpromazine and neutralizing antibodies inhibits the spread of JC virus (JCV) in a tissue culture model: Implications for prophylactic and therapeutic treatment of progressive multifocal leukencephalopathy", *Journal of Neurovirology*, 7(4): 307-310 (2001).

* cited by examiner

*Primary Examiner* — Agnieszka Boesen
(74) *Attorney, Agent, or Firm* — Merchant & Gould P.C.

(57) ABSTRACT

A human neutralizing monoclonal antibody is directed against the VP1 protein of JC virus. The JC virus is responsible for progressive multifocal leukoencephalopathy (PML). The antibody is used in a therapeutic or prophylactic treatment of a JCV infection or of a disease associated with a JCV infection, such as pro¬gressive multifocal leukoencephalopathy (PML). The antibody is also used in the diagnosis of JCV infections or of diseases associated with JCV infections.

10 Claims, 2 Drawing Sheets

FIG.3 alanine scanning VP1

FIG.4

SEQUENCE LISTING

```
<160> NUMBER OF SEQ ID NOS: 12

<210> SEQ ID NO 1
<211> LENGTH: 121
<212> TYPE: PRT
<213> ORGANISM: Homo sapiens

<400> SEQUENCE: 1

Trp Gly Pro Gly Leu Val Lys Pro Ser Gln Ser Leu Ser Leu Thr Cys
1               5                   10                  15

Ala Val Ser Gly Ala Ser Val Ser Ser Gly Ile Asn Tyr Trp Ser Trp
            20                  25                  30

Ile Arg Leu Tyr Pro Gly Lys Gly Leu Glu Trp Ile Gly Tyr Val Tyr
        35                  40                  45

Ser Ser Gly Thr Thr Tyr Tyr Asn Pro Ser Leu Lys Ser Arg Val Ser
    50                  55                  60

Ile Ser Leu Asp Thr Ser Lys Asn Gln Phe Ser Leu Asn Leu Arg Ser
65                  70                  75                  80

Val Thr Ala Ala Asp Thr Ala Val Tyr Tyr Cys Ala Arg Asp Arg Gly
                85                  90                  95

Asp Ser Ser Gly Ser Ser Tyr Tyr Lys Tyr Tyr Met Asp Val Trp Gly
            100                 105                 110

Lys Gly Thr Thr Val Thr Val Ser Ser
        115                 120

<210> SEQ ID NO 2
<211> LENGTH: 105
<212> TYPE: PRT
<213> ORGANISM: Homo sapiens

<400> SEQUENCE: 2

Val Met Thr Gln Ser Pro Ser Ser Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Arg Thr Phe
                85                  90                  95

Gly Gln Gly Thr Lys Val Glu Ile Lys
            100                 105

<210> SEQ ID NO 3
<211> LENGTH: 363
<212> TYPE: DNA
<213> ORGANISM: Homo sapiens

<400> SEQUENCE: 3
tggggcccag gactggtgaa gccctcacag tccctgtccc tcacctgcgc tgtctctggt      60
gcctccgtca gcagtggtat taattactgg agctggatcc gcctctaccc agggaagggc     120
ctggagtgga ttggctatgt gtattccagt gggactacgt actacaaccc gtccctcaag     180
```

```
agtcgagttt ccatatcact agacacgtct aagaaccagt tctccctgaa cctgaggtct    240
gtgactgccg cggacacggc cgtgtattac tgtgcgagag ataggggga tagctcgggg    300 agttcctact acaagtacta catggacgtc tggggcaaag ggaccacggt caccgtctcc    360
tca                                                                  363
```

```
<210> SEQ ID NO 4
<211> LENGTH: 315
<212> TYPE: DNA
<213> ORGANISM: Homo sapiens

<400> SEQUENCE: 4
```

```
gtgatgaccc agtctccatc ctccctgtct gcatctgtag gagacagagt caccatcact    60
tgccgggcaa gtcagagcat tagcagctat ttaaattggt atcagcagaa accagggaaa   120
gcccctaagc tcctgatcta tgctgcatcc agtttgcaaa gtggggtccc atcaaggttc   180
agtggcagtg gatctgggac agatttcact ctcaccatca gcagtctgca acctgaagat   240
tttgcaactt actactgtca acagagttac agtacccctc gaacgttcgg ccaagggacc   300
aaggtggaaa tcaaa                                                     315
```

```
<210> SEQ ID NO 5
<211> LENGTH: 21
<212> TYPE: DNA
<213> ORGANISM: Artificial Sequence
<220> FEATURE:
<223> OTHER INFORMATION: SEQGz primer

<400> SEQUENCE: 5
```

```
gtcgttgacc aggcagccca g                                              21
```

```
<210> SEQ ID NO 6
<211> LENGTH: 21
<212> TYPE: DNA
<213> ORGANISM: Artificial Sequence
<220> FEATURE:
<223> OTHER INFORMATION: SEQKb primer

<400> SEQUENCE: 6
```

```
atagaagttg ttcagcaggc a                                              21
```

```
<210> SEQ ID NO 7
<211> LENGTH: 354
<212> TYPE: PRT
<213> ORGANISM: JC virus

<400> SEQUENCE: 7
```

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95
```

-continued

```
Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Lys Tyr Gly Gln Leu Gln Thr Lys
            340                 345                 350

Met Leu

<210> SEQ ID NO 8
<211> LENGTH: 30
<212> TYPE: DNA
<213> ORGANISM: Artificial Sequence
<220> FEATURE:
<223> OTHER INFORMATION: PCR Fw primer

<400> SEQUENCE: 8
gttttagtaa gcagcatcta tagcagatac                                  30

<210> SEQ ID NO 9
<211> LENGTH: 33
<212> TYPE: DNA
<213> ORGANISM: Artificial Sequence
<220> FEATURE:
<223> OTHER INFORMATION: PCR Rev primer

<400> SEQUENCE: 9
tgacttacta aaacccctaa gatgctcatc tgg                               33

<210> SEQ ID NO 10
<211> LENGTH: 39
<212> TYPE: DNA
<213> ORGANISM: Artificial Sequence
```

```
<220> FEATURE:
<223> OTHER INFORMATION: PCR Fw primer

<400> SEQUENCE: 10
cactctaatg ggcaaggaac tcatgccgct ggtggaggg                    39

<210> SEQ ID NO 11
<211> LENGTH: 30
<212> TYPE: DNA
<213> ORGANISM: Artificial Sequence
<220> FEATURE:
<223> OTHER INFORMATION: PCR Rev primer

<400> SEQUENCE: 11
cttgcccatt agagtgcaca ttcatcaaac                              30

<210> SEQ ID NO 12
<211> LENGTH: 8
<212> TYPE: PRT
<213> ORGANISM: Artificial Sequence
<220> FEATURE:
<223> OTHER INFORMATION: FLAG tag

<400> SEQUENCE: 12

Asp Tyr Lys Asp Asp Asp Asp Lys
1               5
```

HUMAN MONOCLONAL ANTIBODY AGAINST THE VP1 PROTEIN OF JC VIRUS

This application is a National Stage Application of PCT/IB2013/055257, filed 26 Jun. 2013, which claims benefit of Serial No. TO2012A000570, filed 27 Jun. 2012 in Italy and which applications are incorporated herein by reference. To the extent appropriate, a claim of priority is made to each of the above disclosed applications.

BACKGROUND OF THE INVENTION

The present invention is within the immunology field and particularly the field of neutralizing antibodies directed against antigens of virus pathogens.

More specifically, the invention relates to a monoclonal antibody directed against the VP1 protein of JC virus (JCV).

JC virus (JCV) is a human polyomavirus of the Polyomaviridae family and the agent responsible for an extremely serious, often lethal, demyelinating disease designated as progressive multifocal leukoencephalopathy (PML). JC virus has an envelope-less icosahedral capsid that encloses a circular double-stranded DNA genome. The major capsid component is the viral protein VP1. Structural studies done on virions revealed that the polyomavirus capsid is made of 72 pentamers formed by VP1 monomers linked through the C terminal end. VP1 binds to the receptors on target cells and thereby starts infection.

JC virus infects over 85% of adult humans. After the primary infection, JC virus stays quiescent in the kidneys and lymphoid organs. In healthy individuals this virus can replicate in kidney tubule cells and is excreted in the urine, without causing any disease. However, in cases of serious immuno-depression, in subjects who received an organ transplant, in oncologic patients, in patients treated with the novel monoclonal antibody-based immunomodulatory therapies, or in people suffering from AIDS, JC virus can spread to the central nervous system and cause progressive multifocal leukoencephalopathy (PML). In the pre-cART (combination antiretroviral therapy) era, PML incidence in HIV patients ranged from 0.3% to 8%, but the extensive use of antiretroviral treatments determined a significant decrease thereof. HIV infection is the immunodeficiency cause still most frequently associated to PML, with approximately 80% of cases, followed by hematologic tumors (approximately 8%), solid tumors (approximately 3%), organ transplants, and autoimmune diseases treated with immunomodulators.

However, in the last ten years increasing numbers of PML cases non-HIV/AIDS-correlated were reported. Many of these new cases occur in individuals subjected to immunotherapies with recently available drugs. By Feb. 29, 2012, 212 cases of PML connected with natalizumab treatment have been documented, with respect to 99571 patients suffering from multiple sclerosis treated throughout the world with this drug. PML has also been correlated to other immunomodulatory therapies, including efalizumab, mycophenolate mofetil, and rituximab.

For treatment of PML, several therapeutic strategies have been attempted, which were directed against different viral replication cycle phases, such as for example entry into the target cell and replication of the genome. However, none of them gave significant beneficial effects. On the basis of a connection between PML and serious immuno-depression conditions, immunological approaches were also attempted. For instance, patients suffering from PML with a more favorable prognosis were shown to be characterized by a stronger JCV-specific cell-mediated and humoral response. The potential importance of a specific anti-JCV response, particularly against VP1, was confirmed by the strong neutralizing activity of animal (rabbit) sera immunized with the JCV VP1 protein (Goldmann C et al. Journal of Virology, May 1999, pages 4465-4469).

An alternative therapy based on anti-JCV antibodies could thus be applied to treatment of patients suffering from PML. Particularly, in view of the key role of VP1 protein in the early phases of JCV infection, the best candidates could be antibodies against the JCV VP1 protein.

Such a need has now been met by the present inventors who, for the first time, succeeded in obtaining fully human monoclonal antibodies directed towards the JCV VP1 protein and having a neutralizing activity against the virus, which makes them suitable for use in the therapeutic treatment of PML.

These results are to be considered new and surprising in the light of the state of the art, as no human anti-JCV VP1 monoclonal antibody has been so far described, least of all a human anti-JCV VP1 neutralizing monoclonal antibody.

Goldmann C et al. supra, described hyper-immune sera with rabbit anti-VP1 antibodies evoked by virus-like particles having neutralizing properties against JCV.

The Japanese patent application JP9067397A mentioned a method for obtaining a neutralizing anti-JCV antibody, which comprises immunizing rats with a synthetic peptide corresponding to a portion of the VP1 protein, collecting the immune sera from the rats, and separating a fraction of gamma-globulins. In this patent the selection of a monoclonal antibody was not mentioned, least of all one derived from man.

The anti-JCV VP1 monoclonal antibody designated as ab34756, marketed by Abcam®, United Kingdom, is a murine antibody used for detecting the virus through ELISA and Western Blot, clearly not suitable for therapeutic applications, least of all in the human being.

Therefore, none of the anti-JCV antibodies of the prior art would potentially be suitable to be used in therapeutic or prophylactic applications for JCV infections or diseases correlated with the same in human patients.

It is also to be pointed out that, before the testing done by the present inventors, the person of skill in the art reasonably would not have expected to obtain fully human anti-JCV monoclonal antibodies capable of neutralizing JC virus, as no scientific publication was available wherein the presence of neutralizing anti-JCV antibodies had been assessed accurately in the human humoral response. By way of example, the paper by G. Bloomgren et al. N Engl J Med 2012; 366: 1870-80 is mentioned, wherein the authors propose a risk stratification for PML in patients suffering from multiple sclerosis. For the risk stratification, the authors propose three risk factors, that is the presence or absence of anti-JCV antibodies, the previous use of immunosuppressants, and the length of treatment with natalizumab, but they do not propose or mention in any way the assessment of the presence of neutralizing antibodies in the human humoral response. On the other hand, the prior art points out the technical problems connected with the detection of the humoral anti-JCV response in the human being, for instance in Raphael P. Viscidi and Barbara Clayman, Advances in experimental medicine and biology 2006; 577( ): 73-84 and in Wendy A. Knowles, Advances in experimental medicine and biology 2006; 577( ): 19-45.

SUMMARY OF THE INVENTION

Thus, a first object of the present invention is a monoclonal antibody against the VP1 protein of JC virus, characterized by the fact that it is a human antibody and is capable of neutralizing the JC virus.

Within the scope of the present description, the term "monoclonal antibody" is intended to mean any peptide structure capable of binding the antigen, in this case the JCV VP1 protein. This term thus includes both full-length immunoglobulins and functional immunoglobulin fragments, which generally comprise a heavy chain variable domain and a light chain variable domain, but may also comprise a single variable domain. Specific, but not limiting, examples of functional immunoglobulin fragments are the Fab, Fab', F(ab')$_2$, Fv fragments, single chain antibodies (scFv), and single domain antibodies. Single chain antibodies for example are constructed according to the method described in the U.S. Pat. No. 4,946,778 patent to Ladner et al. Single chain antibodies comprise the light and heavy chain variable regions linked through a flexible binding moiety (linker). The antibody fragment designated as single domain antibody is even smaller than the single chain antibody, as it comprises an isolated single VH domain. Techniques for obtaining single domain antibodies with at least partially the same binding ability as the full-length antibody, are described in the prior art and are within the skills of the person of ordinary skill in the art. Ward, et al., in "Binding Activities of a Repertoire of Single Immunoglobulin Variable Domains Secreted from *Escherichia coli*, Nature 341: 544-6, describe a screening method for obtaining an antibody's heavy chain variable region (VH single domain antibody) having an affinity for the target epitope strong enough to bind thereto in an isolated form.

The term "immunoglobulin", as used in the present description, comprises IgG (including IgG1, IgG2, IgG3, IgG4), IgA, IgM, IgD and IgE, both in monomeric and polymeric form.

The term "neutralizing the JC virus" or "capable of neutralizing the JC virus" means that the monoclonal antibody object of the invention is able to block the JC viral replication cycle in one of its phases, thereby affecting its biological activity and at least one of the diseases associated therewith.

In a preferred embodiment, the anti-JCV monoclonal antibody of the invention is capable of binding to a conformational epitope of the JCV VP1 protein, comprising at least one amino acid residue of the primary sequence of the JCV VP1 protein selected from the group consisting of I62, S65, A127, D130, N131, A133 and A175, or any combination thereof. In a more specific embodiment, the conformational epitope comprises the amino acid residues I62, S65, A127, D130, N131, A133 and A175 of the primary sequence of the JCV VP1 protein.

The numbering of the amino acid residues is based on the numbering of the amino acid sequence of the VP1 protein from Mad1 strain (SEQ ID NO: 7). SEQ ID NO:7 is available at the UniProtKB/Swiss-Prot database (Swiss ID: P03089 feature identifier: PRO_0000115021).

The term "conformational epitope" is intended to mean all the amino acid residues, even if not contiguous in the protein's primary sequence, which are directly involved in the binding with the antibody or, if mutated so as not to change the general conformation of the protein, affect all the same the binding affinity of the antibody itself.

In a further preferred embodiment, the monoclonal antibody of the invention comprises at least a heavy chain variable domain and a light chain variable domain, wherein the heavy chain variable domain has the sequence SEQ ID NO:1 (or is encoded by the sequence SEQ ID NO:3) and the light chain variable domain has the sequence SEQ ID NO:2 (or is encoded by the sequence SEQ ID NO:4). Such a specific monoclonal antibody is also called GRE1.

Another aspect of the present invention is a human monoclonal antibody directed against the VP1 protein of JC virus as defined previously, for use in the therapeutic or prophylactic treatment of a JCV infection or a disease associated with a JCV infection, preferably the progressive multifocal leukoencephalopathy (PML).

Identifying the effective dose and formulating the monoclonal antibody of the invention into a pharmaceutical composition suitable for use within the scope of the present invention are within the skills of the person of ordinary skill in the art, without undue inventive efforts.

The monoclonal antibody of the present invention is also suitable to be used in the diagnostic field, as it is characterized by high sensitivity and specificity. This monoclonal antibody showed high affinity (approximately 1 nM) for recombinant VP1 from Mad1 strain, and at the same concentration as a commercial murine antibody (Abcam®), shows a highly improved signal by ELISA. Even when assessed by an immunofluorescence assay performed on JCV-infected (Mad4 strain) COS-7 cells, the antibody showed higher sensitivity and specificity compared to the commercial Abcam® antibody. Moreover, it is important to point out that the monoclonal antibody of the present invention showed no reactivity towards recombinant BKV VP1 (virus belonging to the Polyomaviridae family as JCV; JCV and BKV VP1s exhibit approximately 75% of nucleotide sequence homology) by ELISA, thereby indicating its high specificity uniquely for JCV VP1.

Thus, an in vitro diagnostic method and the relevant kit for the diagnosis of a JCV infection, wherein the monoclonal antibody of the present invention is used as a JCV-specific diagnostic reagent, are within the scope of the present invention.

The in vitro immunodiagnostic method comprises the step of contacting a biological sample from a patient suspected of being infected by JCV with the monoclonal antibody of the invention, under suitable conditions for the monoclonal antibody of the invention to bind to the JCV VP1 antigen, if present in the sample, and the step of qualitatively and quantitatively detecting the binding between the monoclonal antibody of the invention and the JCV VP1 antigen.

The immunodiagnostic method of the invention is for example carried out as an ELISA immunoenzymatic assay or as an immunofluorescence assay. The sample on which the assay is performed is for example a blood, plasma, serum, urine, cephalo-rachidic liquid, biopsy, or any other biological sample deemed suitable.

The immunodiagnostic kit for carrying out the method comprises the monoclonal antibody of the invention, as the specific reagent, and instructions for performing the assay, as well as eventually other components that will vary depending on the type of assay, and are per se known to the person of skill in the art. Examples of additional components that can optionally be contained in the kit are means for the qualitative and/or quantitative detection of the successful binding between antibody and antigen, one or more solid supports (such as for example microtiter plates), a blank solution, one or more standard solutions containing known amounts of the antigen of interest, control solutions, dilution solutions of the sample to be tested, a detection antibody conjugated with a detectable marker (for example a fluorescent molecule) or with an enzyme capable of reacting with a substrate forming a detestable product, buffer washing solutions, solutions containing the enzyme substrate, stop solutions, etc.

The method and kit of the invention can usefully be used for stratifying the risk of developing PML in patients with diverse predisposing conditions.

The examples that follow illustrate the identification and characterization of a human neutralizing monoclonal antibody within the scope of the present invention, as well as the characterization of the epitope recognized by the said antibody. These examples are provided solely by way of illustration, and with no limiting intention, of the scope of the invention as defined in the appended claims.

BRIEF DESCRIPTION OF THE DRAWINGS

FIG. 3 shows the results of a Dot Blot assay performed both with denatured VP1 and wild-type VP1, stained with the murine antibody Abcam and the human monoclonal antibody GRE.

FIG. 4 is a bar graph showing the binding percentages of the murine antibody Abcam and the human monoclonal antibody GRE to JCV VP1 protein subjected to alanine scanning site-directed mutagensis.

DETAILED DESCRIPTION OF THE PREFERRED EMBODIMENT

Example 1

Figure 1:
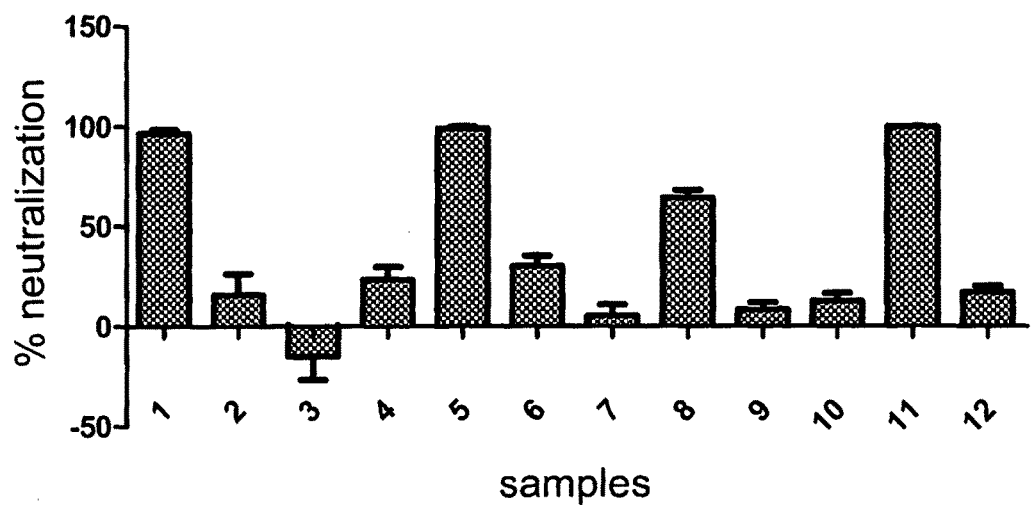
FIG. 1 is a graph illustrating the percentages of the anti-JCV neutralizing activity of sera that had previously demonstrated by ELISA a reactivity >1 O.D. 450 towards VP1.

A combinatorial phage display library of human antibody fragments (monovalent Fabs), of IgG1/k isotype and with an estimated size of 2×10$^7$ elements, was constructed in the pPD phagemid vector through methods similar to those previously described (Plaisant, P., et al., *Human monoclonal recombinant Fabs specific for HCV antigens obtained by repertoire cloning in phage display combinatorial vectors*. Res Virol, 1997. 148(2): p. 165-9). The library was generated from the bone marrow of a 68 year old man whose serum had been tested positive for the presence of anti-VP1/JCV antibodies by ELISA. The ELISA was performed by coating a 96-well plate with 100 ng/well of recombinant JCV VP1 protein (Mad1, Abcam®) in phosphate buffered saline (PBS). Several serum dilutions were added in duplicate to a VP1-coated plate. The plate was incubated at 37° C. for 1 hour and then washed with 0.1% PBS/TWEEN 20. The bound antibodies were detected with an anti-human IgG1 antibody conjugated with peroxidase (HRP) (Sigma-Aldrich®).

The biopanning of the phage-expression combinatorial antibody library for selecting the anti-VP1 antibody was carried out as previously described (Williamson, R. A., et al., *Human monoclonal antibodies against a plethora of viral pathogens from single combinatorial libraries*. Proc Natl Acad Sci USA, 1993. 90(9): p. 4141-5). Briefly, a phage preparation (0.1 ml/well) at a concentration of $10^{12}$ phages per milliliter was used in each of the biopanning cycles for selecting the antibody on high-binding ELISA plates (Costar®) coated with VP1 from Mad1 strain. A total of 5 biopanning cycles were carried out and the phages obtained from the last 3 cycles were converted into a phagemid system expressing soluble Fabs.

*Escherichia coli* cells from the XL-1-blue strain (Agilent Technologies®), transformed with a Fab expression vector, were used for producing the selected Fab molecules for further characterization. Briefly, Fab preparations were obtained by freeze-thaw procedures from a culture. Five ml of SB (super broth) containing ampicillin (50 μg/ml; Sigma-Aldrich®) were inoculated with the transformed bacteria and grown for 7 hours at 37° C. in a rotating stirrer. Isopropyl-β-D-thiogalactopyranoside (IPTG, 1 mmol/l; Sigma-Aldrich®) was added to the growing bacteria, which were further incubated overnight at 30° C. Then, the cells were centrifuged, resuspended in 1 ml of PBS/1% bovine serum albumin (BSA), and subjected to a freeze-thaw procedure (3 rounds). The cell debris was reduced to a pellet by centrifugation at 13000 g at room temperature in a microfuge, and the supernatant was used in an ELISA assay with no further processing. The ELISA was performed as previously described.

Clones that yielded $OD_{450}$>0.8 by ELISA against JCV VP1 were considered positive and further characterized.

105 clones were analyzed, 11 clones tested positive (10.5%). No reactivity was demonstrated against BSA.

In order to confirm the specificity of the positive clones by ELISA, these were tested by an immunofluorescence assay on COS-7 cells (Transformed African Green Monkey Kidney Fibroblast Cells) infected with the Mad4 JCV strain (the recombinant VP1 protein from Mad1 strain was used in the ELISA). A goat anti-human Fab antiserum conjugated with fluorescein isothiocyanate (Sigma-Aldrich®) was used as the secondary antibody. All the ELISA-tested positive clones were confirmed capable of binding to infected cells, whereas no reactivity was detected with uninfected cells. The ELISA-tested negative clones were not able to bind to infected cells.

The nucleic acid from the ELISA-tested positive clones was obtained with the Spin Miniprep kit (Qiagen®) and was sequenced on a 373A sequencer (PerkinElmer). For sequencing the heavy chain, the primer SEQGz (5'-GTCGTTGACCAGGCAGCCCAG-3') (SEQ ID NO:5), which binds to the (+) strand, was used. For the light chain, the primer SEQKb (5'-ATAGAAGTTGTTCAGCAGGCA-3') (SEQ ID NO:6), which binds to the (+) strand, was used. The sequence analysis was carried out with the BLAST and IMGT tools and showed that all the clones derive from the same subfamily of VH genes for the heavy chain, and Vk genes for the light chain, and share the same sequence. Furthermore, the DNA sequence of the antibody is new. It is also important to point out that in literature no human antibody has been so far described that is directed against JCV VP1 protein. Therefore, this is the first human anti-JCV VP1 monoclonal antibody to be described. This antibody has been identified by the name GRE1.

In order to test the neutralizing activity of the human anti-VP1 GRE1 antibody, $5\times10^4$/well COS-7 cells were seeded in complete DMEM medium in a 24-well plate (Corning®). COS-7 are cells permissive to infection by JCV.

The following day, approximately 100 focus forming units of JCV (Mad4 strain) were added to 100 μl of progressive dilutions of GRE1 (two-fold dilutions, from about 20 μg/ml to 0.3 μg/ml). The mixture was incubated for 1 hour at 37° C. and then added to COS-7 cells. Afterwards, they were incubated for 2 hours at 37° C. After one wash with PBS, 500 μl of fresh medium were added to each well and the cells were incubated for 6 days at 37° C.

Assessment of the Neutralizing Activity

The neutralizing activity of the antibodies was assessed by immunofluorescence. Briefly, the immunofluorescence was carried out at 6 days post-infection. The slides were prepared by fixing the cells for 15 min with a Methanol/Acetone mixture (1:1 ratio) at room temperature and by using the commercial Abcam® murine anti-VP1 antibody (1 µg/ml) as the primary antibody, and the FITC-conjugated murine anti-Fab (Sigma-Aldrich®) as the secondary antibody, following the guidelines of the manufacturer.

The assessment is done by comparing the numbers of positive cells in the wells in which the virus was added to GRE1, with cells infected in the absence of the antibody (100% infection).

The data observed under the fluorescence microscope were also confirmed by a robotized fluorescence reading system (IN Cell Analizer Sistem 1000, GE Healthcare) capable of automatically distinguishing the positive cells from the background, which indicated that the antibody as a Fab fragment was capable of inhibiting by more than 50% JCV infection at a concentration of 1 ng/µl.

Analogous experiments have also experimentally demonstrated that not all the sera from patients reactive against JCV VP1 are able to neutralize the virus.

To that end, about 100 sera were tested by ELISA at a 1:400 dilution (dilution in PBS/1% BSA) to verify the presence of anti-JCV antibodies. In short, the ELISA plate (Costar®) was covered with 25 µl/well of a solution containing 100 ng of recombinant VP1 (Abcam®) and incubated at 4° C. overnight. The following day, the plate was washed with water and blocked with PBS-1% BSA (w/v) for 1 hour at 37° C. Afterwards, 40 µl of a single dilution (1:400 in PBS/1% BSA) of the serum to be tested were added and the plate was then incubated for 1 hour at 37° C. After having done 5 washes with PBS-0.1% Tween 20 (Sigma-Aldrich®), by an automatic washer for ELISA microplates (ETI-System Kasher, DiaSorin), 40 µl/well of the commercial horseradish peroxidase-conjugated anti-human IgG antibody were added (Sigma-Aldrich®), following the indications of the manufacturer. The plate was then incubated for 45 minutes at 37° C. After having done several washes, as previously described, 40 µl of substrate (1:1 solution of $H_2O_2$ and 3,3',5,5'-tetramethylbenzidine, TMB substrate kit, Thermo Scientific) were added to each well, for the enzymatic reaction to occur. After about 15 minutes, the enzymatic activity was blocked by adding 40 µl/well of 1N $H_2SO_4$ (Carlo Erba) and the colorimetric reaction was measured with a spectrophotometer (Model 680 Microplate Reader, Bio-Rad) at a wavelength of 450 nm.

BSA antigen or another suitable antigen was introduced in each experiment as a negative control, whose $O.D._{450}$ was used for detecting a possible non-specific reactivity.

A few sera, which showed reactivity against JCV VP1>1 O.D. 450, were analyzed with a neutralization assay. Briefly, the day before infection, $5 \times 10^4$/well COS-7 cells (permissive to infection by JCV) were seeded in complete DMEM medium in a 24-well plate (Corning®). The following day, 200 µl of the JCV (Mad1)-containing medium were added to 200 µl of the 1:200 dilution of the serum to be tested (the final dilution of the serum is then 1:400, the same dilution used for the ELISA assay). The mixture was incubated for 1 hour at 37° C., and then added to the COST cells. Afterwards, they were incubated for 2 hours at 37° C. After one PBS wash, 500 µl of fresh medium were added to each well and the cells were incubated for 6 days at 37° C.

The neutralizing activity of the tested samples was assessed by indirect immunofluorescence. The slides were prepared by fixing the cells for 15 min with a Methanol/Acetone mixture (1:1 ratio) at room temperature and by using the commercial Abcam® murine anti-VP1 antibody (1 µg/ml) as the primary antibody, and the FITC-conjugated murine anti-IgG (Sigma-Aldrich®) as the secondary antibody, following the guidelines provided by the manufacturer.

The assessment was done by comparing the numbers of positive cells in the wells in which the virus was added to the tested sample, with cells infected in the absence of the sample (100% infection).

This analysis demonstrated that, in spite of the reactivity towards VP1 by ELISA, a non negligible number of sera showed no neutralizing anti-JCV activity. The obtained results are illustrated in the graph in FIG. 1. In the graph of FIG. 1, the percentages of the neutralizing activity of some of the tested sera are reported. All the reported sera demonstrated by ELISA a reactivity >1 O.D.450 towards VP1.

Immunofluorescence and Immunohistochemistry on Biopsy Samples

By using the anti-JCV VP1 GRE1 antibody of the present invention in immunofluorescence and immunohistochemistry assays, the presence of JCV can be determined in biopsy samples. This antibody actually showed high sensitivity and specificity for JCV VP1 protein, while on the contrary showed no reactivity towards BKV VP1.

The biopsy samples may be fresh or fixed or paraffinized samples. In the case of fixed and paraffinized samples, if necessary, the sample is deparaffinized and the antigenicity is restored according to standard procedures. The sample is then incubated at 37° C. for 30 minutes with GRE1 (10 µg/ml in PBS). After the incubation period, the sample is washed 5 times in PBS and then incubated for 30 min at 37° C. with the FITC- or horseradish peroxidase-conjugated anti-human Fab (Sigma-Aldrich®), following the guidelines of the manufacturer. In case of use of the antibody conjugated with horseradish peroxidase, it is necessary to add the substrate (diaminobenzidine, DAB substrate kit, Thermo Scientific), which in the presence of peroxidase produces a brown precipitate that allows to visualize the possible antibody binding.

The evaluation of the assay is carried out by observing the sample under a fluorescence microscope or with an automated fluorescence detection system if the FITC-conjugated antibody is used, or by light microscopy or with an automated imaging system if the horseradish peroxidase-conjugated antibody is used.

Capture ELISA for Detecting JCV in Biological Samples

For carrying out an ELISA assay with the human anti-JCV VP1 GRE1 antibody, an ELISA plate (Costar®) is covered with 25 µl/well of a solution containing 40 ng of the sheep anti-human Fd antibody in PBS (1.6 µg/ml final concentration) and incubated at 4° C. overnight. The following day, the plate is washed with water and blocked with PBS-1% BSA (w/v) for 1 hour at 37° C. Afterwards, 40 µl of GRE1 (final concentration approximately 4 ng/µl in PBS/1% BSA) are added per well and the plate is then incubated for 1 hour at 37° C. After having done 5 washes with PBS-0.1% Tween 20 (Sigma-Aldrich®), by an automatic washer for ELISA microplates (ETI-System Kasher, DiaSorin), 40 µl of several dilutions of the biological sample to be tested (serial 10-fold dilutions, starting from the undiluted up to 1:1000 dilutions) are added to each well. The plate is then incubated for 1 hour at 37° C. After having done several washes, as previously described, 40 µl of a 1:1000 dilution of a commercial murine anti-VP1 antibody (Abcam® diluted in PBS/BSA) are added to each well. The plate is left resting for 1 hour at 37° C. After further washes, 40 µl/well of a polyclonal preparation of goat antibodies are added, which bind the Fc portion of murine IgG and are conjugated with horseradish peroxidase (Anti-Mouse IgG (Fc specific)-Peroxidase antibody produced in goat, Sigma-Aldrich®). The plate is incubated for 45 minutes at 37° C. After 5 washes with PBS-Tween20 carried out as previously described, 40 μl of substrate (1:1 solution of $H_2O_2$ and 3,3',5,5'-tetramethylbenzidine, TMB substrate kit, Thermo Scientific) are added to each well, for the enzymatic reaction to occur. After about 15 minutes, the enzymatic activity is blocked by adding 40 μl/well of 1N $H_2SO_4$ (Carlo Erba) and the colorimetric reaction is measured with a spectrophotometer (Model 680 Microplate Reader, Bio-Rad) at a wavelength of 450 nm.

BSA antigen or another suitable antigen is introduced in each experiment as a negative control, whose $OD_{450}$ is used for detecting a possible non-specific reactivity.

Example 2

Definition of the (Linear or Conformational) Nature of the Epitope Recognized by GRE1 Monoclonal Antibody In order to define the (linear or conformational) nature of the epitope recognized by GRE1 monoclonal antibody, Western Blot and Dot Blot assays were carried out both with the denatured protein and the wild type protein.

Figure 2:
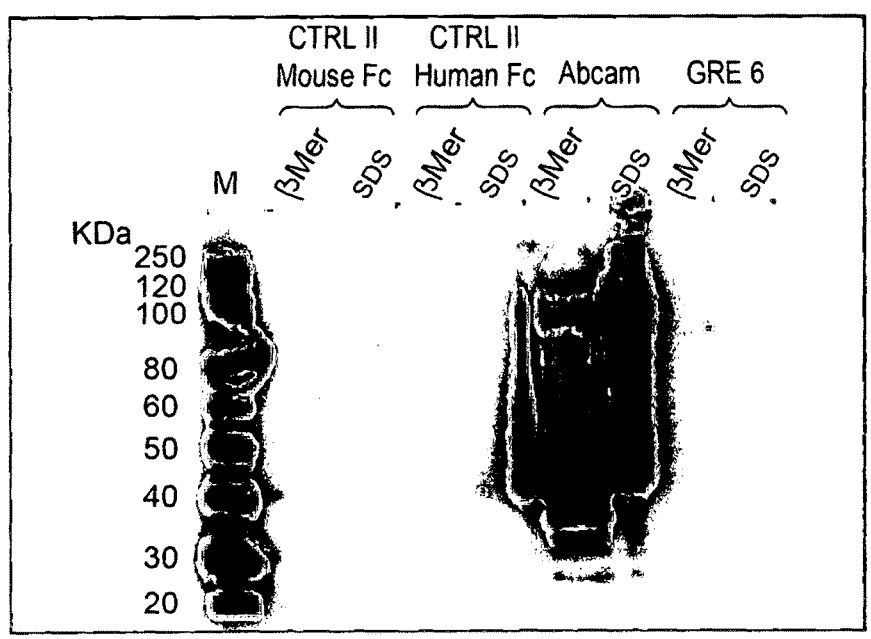
FIG. 2 shows the results of a Western Blot assay under denaturing conditions performed with the JCV VP1 protein stained with the murine antibody Abcam and the human monoclonal antibody GRE.

FIG. 2 shows the results of the Western Blot assay under denaturing conditions. The protein was denatured with β-mercaptoethanol (β-mer) or with sodium dodecyl sulfate (SDS). The commercial murine antibody is designated as Abcam, whereas GRE1 anti-JCV VP1 monoclonal antibody is designated as GRE.

Figures 3, 4:
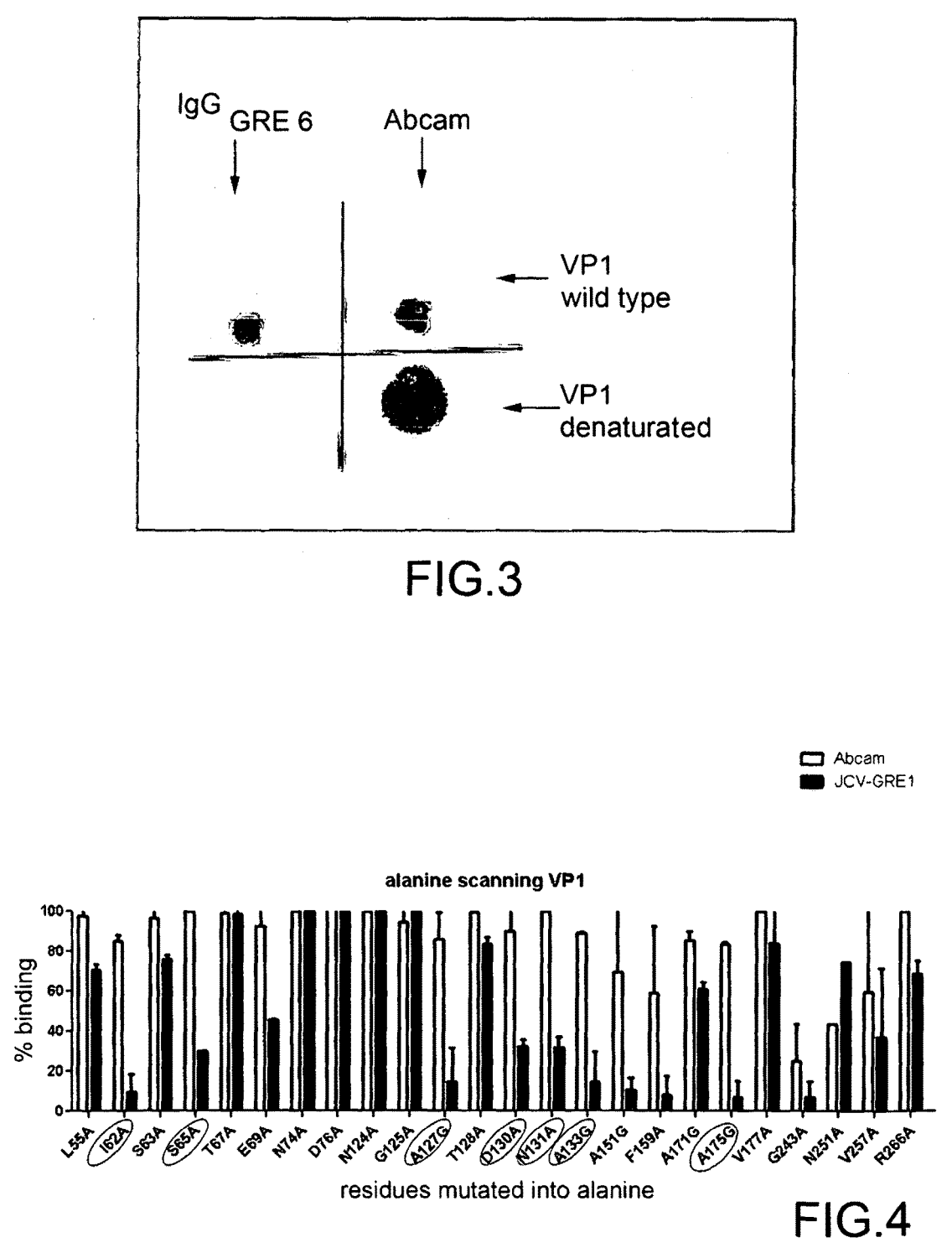

FIG. 3 shows the results of the Dot blot assay performed both with denatured VP1 and VP1 in the wild type conformation. The commercial murine antibody is designated as Abcam, whereas GRE1 anti-JCV VP1 monoclonal antibody is designated as IgG GRE.

The results show that GRE1 is not able to bind to the denatured form of the protein, but that it is only capable of recognizing the non-denatured protein. In corroboration of this fact, a commercial murine antibody (Abcam®, ab34756) directed against a VP1 linear epitope, instead, was able to recognize both of the protein forms. Thus, these results lead to conclude that the epitope recognized by GRE1 monoclonal antibody is a conformational epitope.

Definition of the Specificity of GRE1 Monoclonal Antibody

The high nucleotide sequence homology (approximately 70%) between the BK virus genome (BKV) and the JCV genome, which are the main polyomaviruses capable of infecting man, has been extensively described in the literature.

In order to determine if GRE1 is able to recognize JCV exclusively, its reactivity was tested by an ELISA assay against a recombinant JCV VP1 protein (Abcam®, ab74569) and against the recombinant BKV VP1 protein (Abcam®, ab74567). GRE1 proved to be capable of binding only to the JCV VP1 protein, pointing out its absolute specificity.

Characterization of the Epitope Recognized by GRE1 Monoclonal Antibody by Alanine Scanning Site-Directed Mutagenesis The amino acid sequences of the JCV VP1 and BKV VP1 proteins were aligned by the ClustalX program, so as to identify the portions bearing the residues that show a profound difference (such as charge and polarity) between the two proteins and that may be responsible for the binding difference that the antibody of the invention has towards the two proteins. 33 amino acid residues completely different (as charge and polarity) between the JCV and BKV VP1s were identified through this analysis.

In order to define the critical VP1 residues involved in the binding with GRE1 monoclonal antibody, the previously identified residues were individually mutated into alanine (or into glycine, in the case that the original residue was an alanine). Briefly, the site-directed mutagenesis was performed on the pcDNA™ 3.1 expression vector/V5-His TOPO® TA Expression Kit (Life Technologies™) where the nucleotide sequence encoding the VP1 protein from the Mad1 strain JCV had been previously cloned. The primers used for the mutagenesis were designed to be approximately 30 nucleotides in length and show a 15-20 nucleotide overlapping region at the 5' terminus, in such a way as to obtain an effective mutagenesis product. After the amplification reaction, the PCR product was digested with the enzyme DpnI for 4 hours at 37° C., so as to eliminate the methylated DNA used as the template. After digestion, 1 μL of amplification was used to transform electro-competent cells. A few transformed colonies were isolated and checked by sequencing, in order to analyze if the desired mutation was inserted. Mutated VP1 was then cloned in another expression vector (pCAGEN, Addgene #11160).

HEK 293T (human epithelial kidney) cells were transfected with the pCAG-VP1mut vectors, and the binding of the anti-VP1 antibody to these mutated VP was assessed by FACS (Fluorescence activated cell sorter). In short, HEK293T cells were transfected with 4 μg of vector where mutated VP1 had been cloned. After centrifugation and fixation with 4% paraformaldehyde, the transfected cells were incubated for 30 minutes at room temperature with GRE1 or the Abcam® commercial antibody directed against a C terminus linear sequence, diluted in a permeabilizing solution at a concentration of 1 μg/ml. The cells were then washed and incubated for 30 minutes at room temperature with anti-human or anti-mouse FITC-conjugated monoclonal antibodies, following the indications of the manufacturer (Sigma-Aldrich®) and thereafter analyzed by FACS. The reactivity observed with the non-mutated VP1 protein was considered as 100% binding, instead non-transfected cells were used as the negative control.

The software GraphPad Prism was used for the analysis of the data obtained by FACS and for the graphic editing.

By FACS analysis, it was observed that the residues which, if mutated, disrupt the binding are: I62A, S65A, A127G, D130A, N131A, A133G, A175G (amino acid numbering based on the residues of the Mad1 strain VP1, with the numbering starting from Met at position 1) (FIG. 4). Instead, mutated residues capable of changing the conformation of the protein or drastically decreasing the expression thereof in vitro were not considered in this analysis.

The crystallographic model already described previously in the literature and filed in the free-access RCSB-PDB databank (www.rcsb.org), with the accession code 3NXG (www.rcsb.org/pdb/explore/explore.do?structureId=3NXG) was used for the structural characterization of the epitope recognized by GRE1. The use of this model allowed to notice that residues that are far away on the single monomer, on the contrary are very close on two adjacent monomers in the pentameric form and absolutely contiguous to the portion of the protein involved in the binding with sialic acid. These structural data explain the considerable neutralizing activity of GRE1.

The obtained experimental data show that GRE1 recognizes a conformational, not a linear, epitope comprising at least the following residues: I62, S65, A127, D130, N131, A133, A175 (amino acid numbering based on the residues of the Mad1 strain VP1, with the numbering starting from Met at position 1).

Particularly, it was found that the residues, that if mutated disrupt the binding of GRE1, are very close to the region that is important for the binding between VP1 protein and its receptor, and this explains the neutralizing activity of GRE1.

ELISA Assay for the In Vitro Determination of the Presence of Neutralizing Antibodies in Biological Samples In order to determine the presence of neutralizing antibodies in biological samples (particularly, but not exclusively, in cerebrospinal fluid, serum, or plasma), the epitope recognized by GRE1 (neutralizing antibody) was used in an ELISA assay. The setting-up of a fast and effective detection system was done with two strategies: one of them in which a competitive ELISA assay is carried out with the samples and GRE1, the other one in which the least portion of VP1 (comprising the residues between the positions 50 and 140 of the original protein) that can still be recognized by the neutralizing antibody is used as the antigen. A variant of the latter assay was also set up, wherein the biological samples to be tested were made to compete in the liquid phase against a VP1 that is only mutated in the residues recognized by GRE1, so as to more effectively subtract from the reaction the antibodies capable of recognizing the VP1 portions that are different from those recognized by GRE1.

ELISA Assay for the In Vitro Determination of the Presence of Neutralizing Antibodies by Competition for the VP1 Protein with GRE1 Monoclonal Antibody In order to distinguish GRE1 from the other human antibodies in the biological sample to be tested, GRE1 was labeled by methods of gene expression fusion with the amino acid sequence DYKDDDDK (SEQ ID NO: 12), so as to be exclusively recognized by the commercial monoclonal antibody FLAG® M2 conjugated with horseradish peroxidase (Sigma-Aldrich®).

The ELISA plate (Costar®) was covered with 25 μL/well of a solution containing 300 ng of the recombinant VP1 (Abcam®, ab74569) and incubated at 4° C. overnight. The following day, the plate was washed with water and blocked with PBS-1% BSA (w/v) for 1 hour at 37° C. Afterwards, 40 μL of several dilutions (serial 10-fold dilutions, starting from the undiluted up to 1:1000 dilutions) of the biological sample to be tested were added and the plate was then incubated for 1 hour at 37° C. Thereafter, 40 μl of the GRE1 anti-JCV VP1 antibody (final concentration approximately 1 ng/μL in PBS/1% BSA) were added to each well with the various sample dilutions and the plate was incubated for 30 minutes at 37° C. After having done 5 washes with PBS-0.1% Tween 20 (Sigma-Aldrich®), by an automatic washer for ELISA microplates (ETI-System Kasher, DiaSorin), 40 μL/well of the commercial horseradish peroxidase-conjugated FLAG® M2 antibody were added (Sigma-Aldrich®). The plate was then incubated for 45 minutes at 37° C. After having done several washes, as previously indicated, 40 μL of substrate (1:1 solution of $H_2O_2$ and 3,3',5,5'-tetramethylbenzidine, TMB substrate kit, Thermo Scientific) were added to each well, for the enzymatic reaction to occur. After about 15 minutes, the enzymatic activity was blocked by adding 40 pt/well of 1N $H_2SO_4$ (Carlo Erba) and the colorimetric reaction was measured with a spectrophotometer (Model 680 Microplate Reader, Bio-Rad) at a wavelength of 450 nm.

BSA antigen or another suitable antigen was introduced in each experiment as a negative control, whose $O.D._{450}$ was used for detecting a possible non-specific reactivity.

The difference in absorbance detected in the wells where the monoclonal antibody was added with the different dilutions of the biological sample to be tested and in the wells where the monoclonal antibody was added alone was observed in order to estimate the inhibition of GRE1 binding.

Particularly, if the absorbance in the wells where the monoclonal antibody was added with the different dilutions of the biological sample is lower than the absorbance observed with the monoclonal antibody alone, there has been a competition for epitope binding on VP1 between GRE1 and the antibodies in the sample, thereby indicating the presence of JCV-GRE1-like antibodies in the sample, and thus the presence of neutralizing and protective antibodies.

ELISA Assay for the In Vitro Determination of the Presence of Antibodies in Biological Samples Capable of Recognizing the Same Epitope Bound by GRE1 Monoclonal Antibody In order to determine the minimal portion of VP1 that contains the epitope recognized by GRE1 monoclonal antibody, and yet retains the conformational features, the nucleotide sequence encoding for VP1 from Mad1 strain JCV was digested with DNases so as to obtain randomly cut VP1 sequences. The various VP1 portions were cloned in a phagemid in order to select, through bio-panning against GRE1, the VP1 portion still recognized by the monoclonal antibody. Once the portion still recognized by GRE1 was determined, the fragment was analyzed by specific software to determine the conformation in silico and possibly compare it with the conformation of the full-length VP1 protein.

Taking into consideration the results of this prediction, the selected nucleotide sequence encoding the minimal portion recognized by GRE1, and comprising the residues between positions 50 and 140 of the original protein, was cloned in the bacterial expression vector pET15b, in frame with 6×His-tag and a thrombin cleavage site (pETminiVP1). The restriction sites XhoI and BamHI (present in the vector cloning region, but not within VP1) were used for the cloning. To that end, the VP1 region of interest was amplified by PCR, by inserting respectively the XhoI and BatnHI restriction sites at the 5' and the 3'. The selection of the colonies that contained pETminiVP1 was done on the basis of ampicillin resistance and by sequence analysis.

For the purification of the fragment, one pETminiVP1-containing colony was inoculated in 10 ml of LB with 50 μg/mL ampicillin and grown at 37° C. overnight. The following day, 5 ml of culture were sub-inoculated in 500 ml of LB medium with 50 μg/mL ampicillin. The culture was analyzed at regular intervals with a spectrophotometer to check the bacterial growth. When the culture reached an OD600 of 0.6-1, 0.4 mM isopropyl-β-D-1-thiogalactopyranoside (IPTG) was added to the medium and left stirring at room temperature overnight.

The following day, the bacterial culture was centrifuged for 15 minutes at 3900 rcf, and the bacterial pellet was resuspended in 20 ml of buffer A (50 mM Tris pH 7.5, 5% glycerol, 250 mM NaCl, 30 mM imidazole). The cells were then lysed by using a sonicator. The suspension was centrifuged for 45 minutes at 12,000 rcf and filtered with 0.4 μm filters to eliminate the bacterial debris.

The fragment was then purified by affinity chromatography on a nickel column. Before applying the sample to the column, the resin was washed with 3 volumes of buffer A, 3 volumes of buffer B (20 mM Tris pH 7.5, 5% glycerol, 250 mM NaCl, 500 mM Imidazole) and re-equilibrated with 8 volumes of buffer A. At this time, the sample was run on the column. 50 ml of buffer A were used to wash the column from the unbound sample, and the sample was eluted with a 0%-100% gradient of buffer B. After elution, the column was re-equilibrated with buffer A. Once concentrated, the fragment was digested with thrombin so as to eliminate the histidine tail that could affect the biological sample to be tested. In order to eliminate traces of the elution buffer that could affect a possible use of the purified fragment, the elution was dialyzed against PBS. The quality and the concentration of the fragment, which from now on will be called miniVP1, were analyzed by a 12% SDS gel.

For the ELISA, the 96-well plate (Costar®) was covered with 25 μl/well of a solution containing 300 ng of the miniVP1 fragment (generated as previously described), and incubated at 4° C. overnight. The following day, the plate is washed with water and blocked with PBS-1% BSA (w/v) for 1 hour at 37° C.

At completion of the incubation of the plate, 40 μL of several dilutions (serial 10-fold dilutions, starting from the undiluted up to 1:1000 dilutions) of the biological sample to be tested were added and the plate was incubated for 1 hour at 37° C. After having done 5 washes with PBS-0.1% Tween 20 (Sigma-Aldrich®), by an automatic washer for ELISA microplates (ETI-System Kasher, DiaSorin), 40 μL/well of a polyclonal preparation of horseradish peroxidase-conjugated goat antibodies that bind the Fc portion of human IgG (Sigma-Aldrich®) were added. The plate was incubated for 45 minutes at 37° C. After 5 washes with PBS-Tween20 carried out as previously described, 40 μL of substrate (1:1 solution of $H_2O_2$ and 3,3',5,5'-tetramethylbenzidine, TMB substrate kit, Thermo Scientific) were added to each well, for the enzymatic reaction to occur. After about 15 minutes, the enzymatic activity was blocked by adding 40 μL/well of 1N $H_2SO_4$ (Carlo Erba) and the colorimetric reaction was measured with a spectrophotometer (Model 680 Microplate Reader, Bio-Rad) at a wavelength of 450 nm.

BSA antigen or another suitable antigen was introduced in each experiment as a negative control, whose $O.D._{450}$ was used for detecting a possible non-specific reactivity. GRE1 monoclonal antibody was used as a positive control at a final concentration of 1 ng/A.

Samples that showed a higher reactivity towards miniVP1 compared to BSA were considered positive, and thus containing JCV-GRE1-like antibodies with a neutralizing, and thus protective, activity.

ELISA Assay for the In Vitro Determination of the Presence of Antibodies in Biological Samples Capable of Recognizing the Same Epitope Bound by GRE1 Monoclonal Antibody (a Variant with Competition by a Mutated VP1)

In order to increase the stringency of the previous assay, another version of the experiment was set up, by adding a step of pre-incubating the sample to be tested with a VP1 mutated in the residues that are important for the binding of GRE1 to the protein.

In order to obtain the VP1 protein modified in the GRE1 binding sites, and which will later act by de-selecting antibodies in the biological samples, the site-directed mutagenesis strategy was used by making some changes: since some residues to mutagenize are very close, a few residues were mutated simultaneously. First, the residues 162 and S65 were mutated by using the following primer Fw:

(SEQ ID NO: 8)
5'-gttttagtaagca$\underline{\text{GCa}^{621/A}}$tctata$\underline{\text{Gca}^{65S/A}}$gatac-3' and 5'-tgacttactaaaacccctaagatgctcatctgg-3' (SEQ ID NO:9) as the reverse. The vector pcDNA™ 3.1/V5-His TOPO® TA Expression Kit (Life Technologies), where the VP1 from Mad1 strain JCV had been previously cloned, was used as the template. An amplification product also containing the mutated protein was obtained by PCR. In order to remove the DNA template used for the reaction (which certainly will not contain the desired mutations), the reaction product was digested with DpnI for 4 hrs at 37° C. Thereafter, electro-competent cells were transformed with 2 μL of the previously treated amplification product. Cells containing the plasmid were selected on the basis of ampicillin resistance and then checked by sequence analysis. The vector that showed the mutations inserted with the first amplification reaction was used as the template for the second amplification reaction, where the positions 127A, 130D, 131N, 133A were mutated. In order to insert these mutations, (SEQ ID NO: 10)
5'-cactctaatgggcaa$\underline{\text{gGa}^{127A/G}}$actcat
$\underline{\text{gCc}^{130D/A}\text{GCt}^{131N/A}}$ggt$\underline{\text{gGa}^{133A/G}}$ggg-3' was used as the Fw primer, and 5'-cttgcccattagagtgcacattcat-caaac-3' (SEQ ID NO:11) as the reverse primer. The PCR product was digested with DpnI for 4 hrs at 37° C. Thereafter, electro-competent cells were transformed with 2 μL of the previously treated amplification product. Cells containing the plasmid were selected on the basis of ampicillin resistance and then checked by sequence analysis. The VP1 that by sequence analysis exhibited all of the inserted mutations was cloned in the bacterial expression vector pET15b, in frame with 6×His-tag and a thrombin cleavage site (pET-VP1mut). The mutated VP1 (VP1mut) was then purified with the same protocol as used for the purification of miniVP1.

For the ELISA, the 96-well plate (Costar®) was covered with 25 μL/well of a solution containing 300 ng of miniVP1 (generated as previously described), and incubated at 4° C. overnight. The following day, the plate was washed with water and blocked with PBS-1% BSA (w/v) for 1 hour at 37° C. In the meanwhile, 50 μg/mL of mutated VP1 was preincubated with several dilutions (serial 10-fold dilutions, starting from the undiluted up to 1:1000 dilutions) of the biological sample to be tested and incubated for 30 minutes at 37° C. At completion of the incubation of the plate, 40 μL of the mix of the various serum dilutions (o other biological sample) with the mutated VP1 were added and the plate was incubated for 1 hour at 37° C. After having done 5 washes with PBS-0.1% Tween 20 (Sigma-Aldrich®), by an automatic washer for ELISA microplates (ETI-System Kasher, DiaSorin), 40 μL/well of a polyclonal preparation of horseradish peroxidase-conjugated goat antibodies that bind the Fc portion of human IgG (Sigma-Aldrich®) were added. The plate was incubated for 45 minutes at 37° C. After 5 washes with PBS-Tween20 carried out as previously described, 40 μL of substrate (1:1 solution of $H_2O_2$ and 3,3',5,5'-tetramethylbenzidine, TMB substrate kit, Thermo Scientific) were added to each well, for the enzymatic reaction to occur. After about 15 minutes, the enzymatic activity was blocked by adding 40 μL/well of 1N $H_2SO_4$ (Carlo Erba) and the colorimetric reaction was measured with a spectrophotometer (Model 680 Microplate Reader, Bio-Rad) at a wavelength of 450 nm.

BSA antigen or another suitable antigen was introduced in each experiment as a negative control, whose $O.D._{450}$ was used for detecting a possible non-specific reactivity. JCV-GRE1 monoclonal antibody was used as a positive control at a final concentration of 1 ng/μL.

Samples that showed a higher reactivity towards the miniVP1 peptide compared to BSA were considered positive, and thus containing JCV-GRE1-like neutralizing, and thus protective, antibodies.

The invention claimed is:

1. A recombinant human monoclonal antibody specifically binding VP1 protein of JC virus, wherein the monoclonal antibody is capable of neutralizing the JC virus, the human monoclonal antibody comprising at least a heavy chain variable region and a light chain variable region, wherein the heavy chain variable region has the sequence SEQ ID NO:1 or is encoded by the sequence SEQ ID NO:3 and the light chain variable region has the sequence SEQ ID NO:2 or is encoded by the sequence SEQ ID NO: 4.

2. The monoclonal antibody according to claim 1, which is a full-length immunoglobulin or an antigen-binding fragment thereof selected from the group consisting of Fab, Fab', F(ab')$_2$, Fv, and single chain antibodies (scFv).

3. The monoclonal antibody according to claim 1, for therapeutic or prophylactic treatment of a JCV infection or progressive multifocal leukoencephalopathy (PML) associated with a JCV infection.

4. A pharmaceutical composition comprising a monoclonal antibody according to claim 1.

5. The pharmaceutical composition according to claim 4 for the therapeutic or prophylactic treatment of a JCV infection or progressive multifocal leukoencephalopathy (PML) associated with a JCV infection.

6. An in vitro method of diagnosis of a JCV infection or progressive multifocal leukoencephalopathy (PML) associated with a JCV infection, the method comprising the steps of:
contacting a biological sample from a patient suspected of being infected with JCV with a monoclonal antibody according to claim 1, under suitable conditions for the monoclonal antibody to bind the JCV VP1 protein, if present in the sample, and
qualitatively or quantitatively detecting the binding of the monoclonal antibody to the JCV VP1 protein, said binding being indicative of JCV infection or progressive multifocal leukoencephalopathy (PML) associated with a JCV infection.

7. The method according to claim 6, wherein detecting is performed with an immunological ELISA assay or an immunological fluorescent assay or an immunohistochemical assay.

8. An immunodiagnostic kit for the diagnosis of a JCV infection or progressive multifocal leukoencephalopathy (PML) associated with a JCV infection, the kit comprising a recombinant human monoclonal antibody according to claim 1 and instructions for carrying out an in vitro immunodiagnostic method.

9. An immunodiagnostic kit, the kit comprising a recombinant human monoclonal antibody directed against the VP1 protein of JC virus, wherein the monoclonal antibody is a human antibody and is capable of neutralizing the JC virus, and instructions for carrying out an in vitro immunodiagnostic method, wherein the in vitro immunodiagnostic method is a method according to claim 6.

10. A method of neutralizing the JCV virus in a human patient suffering from a JCV infection, the method comprising administering to a human patient an effective amount of a monoclonal antibody according to claim 1.

* * * * *